United States Patent [19]

Murata

[11] Patent Number: 4,808,172
[45] Date of Patent: Feb. 28, 1989

[54] FIRST-AID ADHESIVE BANDAGE

[75] Inventor: Takaaki Murata, Kumamoto, Japan

[73] Assignee: Aso Pharmaceutical Co., Ltd., Kumamoto, Japan

[21] Appl. No.: 68,307

[22] Filed: Jul. 1, 1987

[30] Foreign Application Priority Data

Jul. 5, 1986 [JP] Japan .................... 61-103298
Jan. 17, 1987 [JP] Japan .................... 62-5159

[51] Int. Cl.⁴ ................................ A61F 7/02
[52] U.S. Cl. .................... 604/306; 128/155
[58] Field of Search ............... 604/306, 307; 128/132 R, 155, 156

[56] References Cited

U.S. PATENT DOCUMENTS

| | | | |
|---|---|---|---|
| 3,366,112 | 1/1968 | Antonik | 604/306 |
| 3,580,254 | 5/1971 | Stuart | 128/268 |
| 4,117,841 | 10/1978 | Perrotta et al. | 128/155 |
| 4,526,176 | 7/1985 | Bremer et al. | 128/641 |
| 4,689,044 | 8/1987 | Murata | 604/306 |

Primary Examiner—Samuel Scott
Assistant Examiner—Allen J. Flanigan
Attorney, Agent, or Firm—Armstrong, Nikaido, Marmelstein & Kubovcik

[57] ABSTRACT

This invention provides a first-aid adhesive bandage comprising a bandage main body 1 having an adhesive surface covered with a peel cover 9, a pad 3 affixed to the main body 1 and a capsule 4 filled with a medicinal agent and supported on or over the pad 3 by the peel cover 9, the top wall 4a of the capsule 4 having a dented portion 7 extending laterally at the center thereof for bending, and a projection 8 extending downward from the center of the dented portion 7 to rupture a thin sheet 5 of capsule bottom, alternatively the top wall 4a having a pair of slanted blades extending from the center of the dented portion 7, the dented portion 7 being intended to facilitate bending of the capsule 4 and to allow the bending to achieve quick and extensive rupture of the thin sheet 5 of capsule bottom.

15 Claims, 4 Drawing Sheets

FIRST-AID ADHESIVE BANDAGE

FIELD OF THE INVENTION

The present invention relates to a first-aid adhesive bandage provided with a capsule having enclosed therein a medicinal agent.

DESCRIPTION OF THE PRIOR ART

Various first-aid adhesive bandages have heretofore been provided. For example, first-aid adhesive bandages are in wide use which comprise a pad of gauze or the like affixed to the central portion of the adhesive bandage main body and dried after having been impregnated with a medicinal agent, and peel paper sheets affixed to the main body to cover the pad and separable therefrom when pulled away from each other. However, these bandages have drawbacks. Although the pad contains a medicinal agent, it is in a dry state, so that the pad is likely to injure the wound and also fails to produce a sterilizing antiseptic effect even when in contact with the wound unless the medicinal agent dissolves out from the pad into the fluid secreted from the wounded portion.

To overcome the prior art deficiencies, we developed a first-aid adhesive bandage which comprises a capsule of suitable shape containing a medicinal solution and mounted on a pad attached to the central portion of upper surface of the adhesive sheet. The proposed first-aid adhesive bandage has the following structure and is used in the manner stated below. When the capsule of the adhesive bandage is depressed from above for use, an aluminum foil or like thin sheet forming the bottom wall of the capsule is ruptured by a projection extending downward from the underside center of top wall of the capsule to draw off the solution from the capsule onto the pad for impregnation. Thereafter the ripped capsule is removed from the pad and the pad is applied to the wound (German patent application published under No. 3432939).

While this structure is advantageous in that the projection formed on the underside of the capsule top wall is able to unmistakably tear the thin sheet of capsule bottom wall, the first-aid adhesive bandage with such structure suffers the following shortcomings. The tear occurs only in the central portion of the thin sheet, giving an opening of small area for releasing the medicinal solution. This hinders quick elimination of the solution from the capsule, involving intensified or repeated application of pressure to discharge the solution to the pad and consequently a portion of the solution is likely to remain in the peripheral part of the capsule, failing to be completely removed.

A European patent application published under No. 0081438 teaches a first-aid adhesive bandage having a sectionally V- or U-shaped shallow recess formed on the top wall of a blister over a pad to facilitate ripping of the thin sheet covering the blister bottom portion. However, the recess is not sufficient in depth because it is formed to prevent the slipping-off of user's finger from its depressing position. The adhesive bandage described therein lacks even the advantage taught by the German application that the projection of the capsule ruptures the thin sheet. Accordingly, when the capsule or blister is depressed to apply a pressure to the solution therein, the pressure of the solution ruptures the weakest portion of the thin sheet, i.e. a peripheral portion of the sheet where the lower edge of the peripheral wall of the capsule or blister is adhered. Consequently, the solution is forced out through this portion over the adhesive surface of the bandage main body or off the surface, failing to properly impregnate the pad for use.

SUMMARY OF THE INVENTION

It is an object of the present invention to overcome the foregoing problems and provide a first-aid adhesive bandage capable of discharging substantially the whole amount of a medicinal solution from a capsule smoothly and quickly onto a pad to impregnate the pad therewith.

Other objects and features of the invention will become apparent from the following description.

The present invention provides a first-aid adhesive bandage comprising a bandage main body having an adhesive coating on its upper surface; a pad affixed to the upper surface of the main body; a capsule containing a medicinal agent and having a bottom wall of a thin sheet; and a peel cover removably attached to the adhesive coating and holding the capsule on or over the pad, the top wall of the capsule having a central portion dented toward the capsule bottom wall to form a groove extending laterally between the opposed side walls of the capsule, and the dented portion having a projection extending downward from its center so as to rupture the thin sheet of capsule bottom when a force is applied to the upper surface of the capsule.

Alternatively the lower end of the dented portion may be defined by a pair of gentle slants each extending upwardly from the center of the dented portion toward the capsule side walls, each slant having an acuate sectional profile to form a blade.

The invention will be described below with reference to the accompanying drawings which are given for illustrative purposes only and to which the invention is not limited.

DESCRIPTION OF THE PREFERRED EMBODIMENTS

Figure 1:
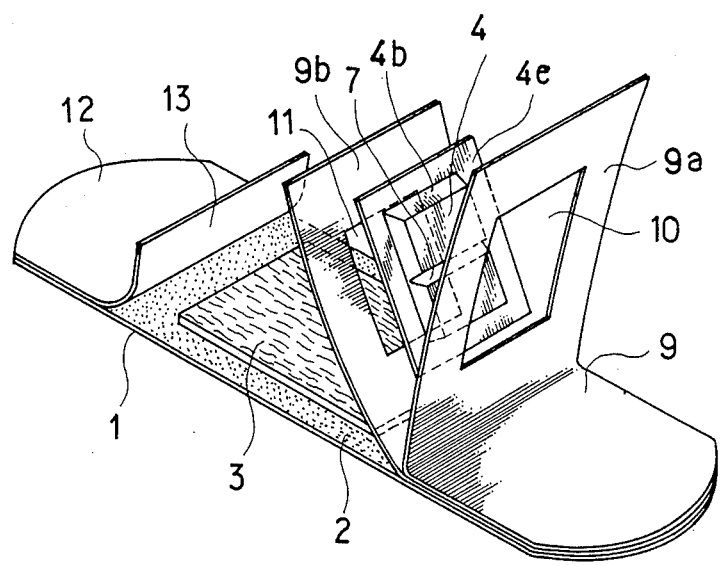
FIG. 1 is a partially exploded perspective view showing an embodiment of the first-aid adhesive bandage according to the present invention.
Figure 2:
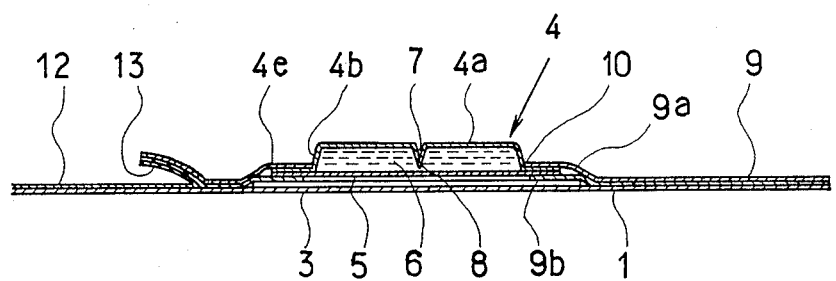
FIG. 2 is a front view in vertical section of the embodiment shown in FIG. 1
Figure 3:
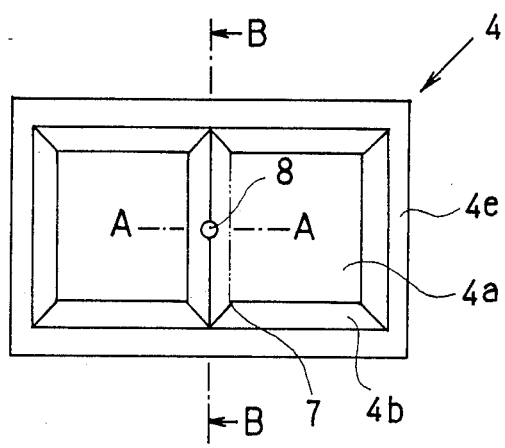
FIG. 3 is a plan view of a capsule in the embodiment shown in FIG. 1.
Figure 4:
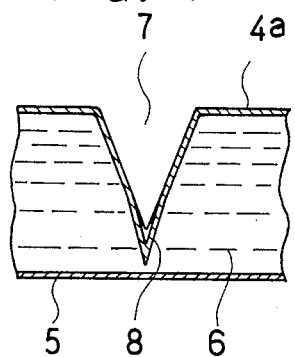
FIG. 4 is a front view in vertical section of the capsule shown in FIG. 3.

FIGS. 1 and 2 show an embodiment of the invention. Indicated at 1 is an adhesive bandage main body, or a rectangular adhesive sheet, having a coating 2 formed by applying an adhesive to the upper surface of a woven or nonwoven fabric, plastics sheet or the like. A pad 3 of gauze, laminated absorbent paper sheets or the like is joined to the central portion of upper surface of the main body 1.

A capsule 4, rectangluar in plan view, is made of a plastic sheet and has a sectionally rectangular, trapezoidal or like shape. The capsule 4 has a top wall a integral with a side wall 4b extending downward from the periphery of the top wall 4a. The side wall 4b is integrated with a flange 4e horizontally outwardly projecting from the lower end of the side wall 4b. The opening at the bottom of the capsule 4 is closed with a thin sheet 5 of aluminum foil, glassine paper or like material which can be ruptured. The thin sheet 5 is adhered at the upper surface of its periphery to the underside of the flange 4e with an adhesive or the like to form the bottom of the capsule 4.

Designated 6 is a medicinal agent liquid-tightly enclosed in the capsule 4 such as a disinfectant, analgesic, hemostatic agent or the like.

Figures 5, 6:
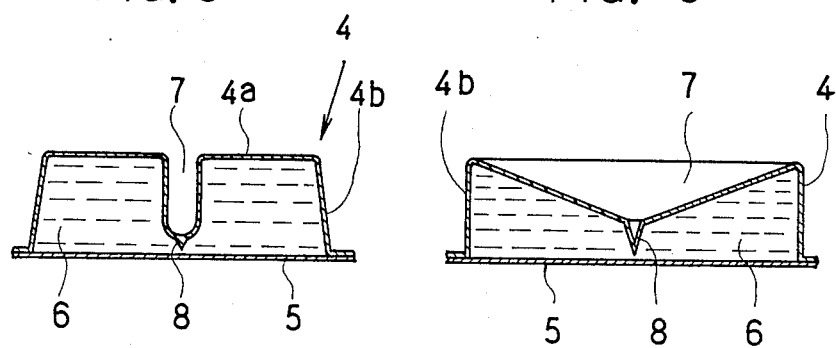
FIG. 5 is a front view in vertical section of another embodiment of the capsule.
FIG. 6 is a side view in vertical section of a further embodiment of the capsule.

The top wall 4a of the capsule 4 has a portion dented at the center toward the capsule bottom to form a sectionally V-shaped groove extending laterally between the opposed side walls 4b, 4b of the capsule. The dented portion 7 optionally may have a U shape in section as shown in FIG. 5. The dented portion 7 illustrated in FIG. 5 includes a conical projection 8 extending downwardly from the center of its lower end. The projection 8 is held in the capsule 4 with its tip in contact with or in proximity to the center of the upper face of the thin sheet 5.

The lower end of the dented portion 7 may have a horizontal bottom outline to provide a groove depth substantially uniform along the whole length, or alternatively may have a bottom outline composed of a pair of gentle slopes and extending outwardly upwardly from the center with the projection 8 toward the side walls of the capsule 4 to provide groove depths each progressively reduced, as shown in FIG. 6. Optionally the capsule 4 may have a polygonal, rounded or any other suitable shape, in either plan view or elevational view, insofar as it has the dented portion 7 and the flange 4e.

A peel cover 9 is removably adhered to the adhesive coating 2 on the adhesive sheet 1 over its area extending from one end thereof to slightly beyond the capsule. The peel cover 9 consists of a pair of peel sheets 9a, 9b made of paper sheets or flexible plastics sheets and suporposed on each other. A layer of silicone or the like is formed on the entire rear side of the underlying peel sheet 9b and is temporarily and removably joined to the coating 2 of the adhesive sheet 1.

In the peel cover 9 to be partly laid on the pad 3 on the adhesive sheet 1, the upper peel sheet 9a is formed with an aperture 10 virtually corresponding in shape to the capsule 4 in plan view, while the lower peel sheet 9b has an aperture 11 identical in size and shape with the aperture 10. The flange 4e of the capsule 4 is interposed between the peel sheets 9a, 9b, and the side wall 4b of the capsule 4 is passed through the retaining aperture 10 to protrude over the peel cover 9. The thin sheet 5 forming the bottom of the capsule 4 is disposed to cover the aperture 11 of the peel sheet 9b and overlies the central portion of upper surface of the pad 3.

The capsule 4 optionally may be adhered to a one-piece peel sheet instead of being fixed in between the peel sheets 9a, 9b. The peel cover 9 may be made of plastics integrally with the capsule 4.

Indicated at 12 is a peel piece removably attached to the remaining end area of upper surface of the adhesive sheet 1. The inner end of the peel piece 12 is folded by a suitable distance for overlapping to form a turn-up end 13. The corresponding end of the peel cover 9 is simply superposed on the turn-up end 13 and remains unadhered thereto so that the peel cover 9 will be readily peeled.

For use of the adhesive bandage with such structure, the bandage is held with its top surface upturned in the user's hand and the capsule 4 is depressed at the top wall 4a by exerting toward the pad 3 a force in a way to fold into two the capsule 4 with the pad 3, whereby the capsule 4 is easily and instantly bent at the dented portion 7 to cause the projection 8 on the underside center of the dented portion 7 to rupture the central point of thin sheet 5 at the bottom of the capsule 4. Upon rupture, the medicinal agent in the capsule 4 is discharged out of the broken portion of thin sheet 5 onto the pad 3 while the opening in the broken portion is rapidly enlarged, becoming ready to accept a larger flow of the agent. The capsule 4 is bent at the dented portion 7 and the two capsule portions on either side of the dented portion 7 are each upwardly slanted with the ends held upward so that the medicinal agent including the portion locally existing in the periphery of the capsule 4 is permitted to rush toward the opening over parts of thin sheet 5, whereby the agent is smoothly and quickly drawn off for virtually complete removal.

The medicinal agent 6 thus discharged and flowed into the pad 3 comes into contact with the underside of the peel cover 9 but remains unabsorbed in the underlying peel sheet 9b having its rear side coated with silicone so that the whole agent can be permeated into the pad 3.

After the medicinal agent in the capsule 4 has been drawn off and permeated into the pad 3 in this way, the peel cover 9 is peeled, the pad 3 is applied to the wound, and the adhesive sheet is attached to the skin portion surrounding the wound. Since the forward end of the peel cover 9 is laid over the turn-up end 13 of the peel piece 12 as stated above, the peel cover 9 and the peel piece 12 can be easily peeled together by pulling these ends away from each other. After peeling, it is possible to dispose of the empty capsule 4 together with the peel cover 9 remaining attached thereto.

Figure 7:
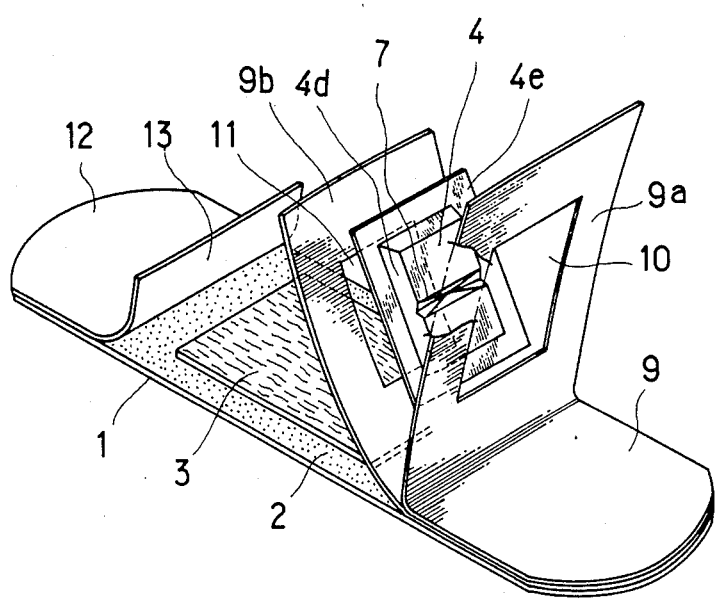
FIG. 7 is a partially exploded perspective view of another embodiment of the first-aid adhesive bandage according to the present invention.
Figure 8:
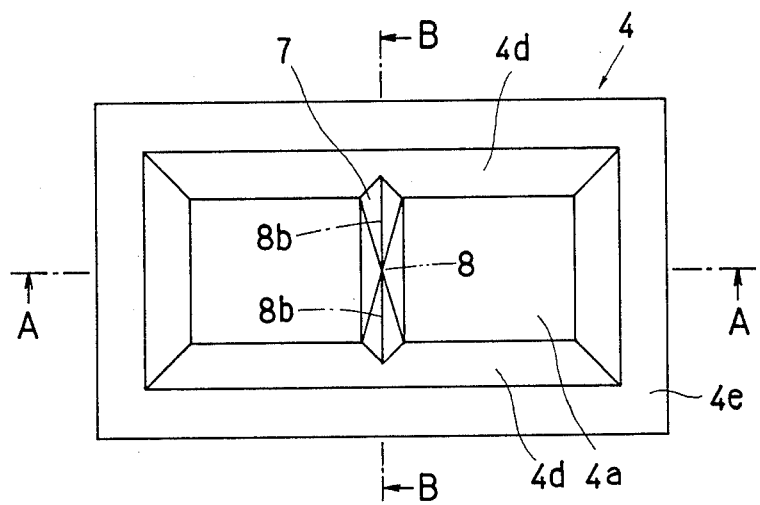
FIG. 8 is a plan view of a capsule in the embodiment shown in FIG. 7.
Figure 9:
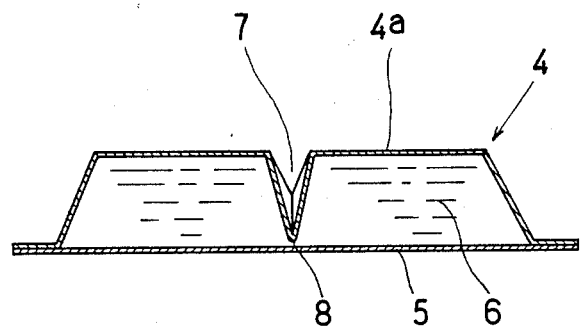
FIG. 9 is a front view in vertical section of the capsule shown in FIG. 8.
Figure 10:
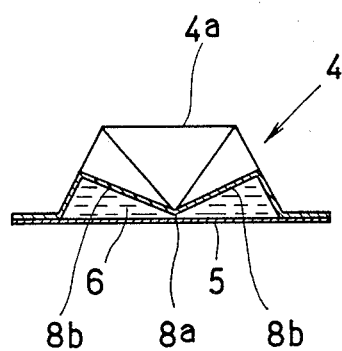
FIG. 10 is a side view in vertical section of the capsule shown in FIG. 8.

Another embodiment of the present invention is shown in FIG. 7 in which like reference characters denote like parts or members in the various views. While the adhesive bandage according to the first-mentioned embodiment has the top wall 4a of the capsule 4 dented at the center to form a V-shaped groove extended laterally between the opposed side walls 4d, 4d of the capsule, the embodiment as illustrated in FIG. 7 is different in that the lower end of a dented portion 7 has a pair of gentle slants extending upwardly from a central tip 8a towards capsule side walls 4d, 4d, and having an acuate sectional profile to form blades 8b, 8b, as illustrated in detail in FIGS. 8 to 10. The central tip 8a is held in contact with or in close proximity to the top surface of the thin sheet.

The embodiment of first-aid adhesive bandage depicted in FIG. 7 can be used in the same manner as in the first-mentioned embodiment. Stated more specifically, the top wall 4a of the capsule 4 in FIG. 7 is depressed downward toward the pad 3 in a way to fold the capsule 4, whereby the capsule 4 is easily and rapidly bent at the sectionally V-shaped dented portion 7. In the illustrated embodiment, the central tip 8a of the dented portion 7 then presses and pierces the center of capsule bottom thin sheet 5 whereby the thin sheet is instantly broken, thereby initiating the discharge of the medicinal agent in the capsule onto the pad 3. The opposed slanting blades 8b, 8b further destroy the thin sheet 5 with the rapid progress of bending of the dented portion 7 with the result that the opening of the thin sheet 5 is enlarged to increase the flow of the agent 6 while part of the agent 6 existing locally in the periphery of the capsule interior moves in a swift current toward the opening, achieving a vertually complete removal of the agent in a swift and smooth way. According to this embodiment, the thin sheet is torn by the blades 8b, 8b, thus assuring more extensive and more rapid tear than in the first-mentioned embodiment intended to achieve tear mainly by bending action.

I claim:

1. A first-aid adhesive bandage comprising a bandage main body having an adhesive coating on its upper surface; a pad affixed to the upper surface of the main body; a substantially rectangular, box-like capsule containing a medicinal agent and having a bottom wall of a thin sheet; and a peel cover removably attached to the adhesive coating and holding the capsule on or over the pad, the top wall of the capsule having a central portion dented toward the capsule bottom wall to form a groove extending laterally between opposed side walls of the capsule, and the dented portion having a projection extending downward from its center so as to rupture the thin sheet of capsule bottom when a force is applied to the upper surface of the capsule.

2. A first-aid adhesive bandage according to claim 1 wherein the dented portion of the capsule top wall has a V shape in section.

3. A first-aid adhesive bandage according to claim 1 wherein the dented portion of the capsule top wall has a U shape in section.

4. A first-aid adhesive bandage according to claim 1 wherein the dented portion of the capsule top wall has a lower end having an outline composed of a pair of gentle inclines extending outwardly upwardly toward the side walls of the capsule from the center of the groove with the projection positioned thereunder.

5. A first-aid adhesive bandage according to claim 1 wherein the capsule is rectangular in plan view and has a top wall, side walls and a flange projecting horizontally outwardly from the lower peripheral end of the side walls.

6. A first-aid adhesive bandage according to claim 5 wherein the peel cover has an aperture permitting the top wall and side walls of the capsule to pass therethrough and the capsule is retained on or over the pad with the top wall and the side walls passed through the aperture and the flange of the capsule covered with and supported by the peel sheet.

7. A first-aid adhesive bandage according to claim 5 wherein the peel cover consists of a pair of peel sheets superposed on each other, said upper peel sheet being formed with an aperture permitting the top wall of the capsule and the side walls thereof to pass therethrough and said lower peel sheet having an aperture through which the medicinal agent released from the capsule can flow into the pad, said capsule being retained on or over the pad such that the flange of the capsule is interposed between the upper and lower peel sheets with its top wall and the side walls passed through the aperture of the upper peel sheet.

8. A first-aid adhesive bandage according to claim 1 wherein said peel cover is made of plastics and formed integrally with the said capsule.

9. A first-aid adhesive bandage according to claim 1 wherein the projection for rupture of the thin sheet is formed integrally with the top wall of the capsule.

10. A first-aid adhesive bandage according to claim 1 wherein the projection for rupture of the thin sheet is of conical shape.

11. A first-aid adhesive bandage comprising a bandage main body having an adhesive coating on its upper surface; a pad affixed to the upper surface of the main body; a substantially rectangular, box-like capsule containing a medicinal agent and having a bottom wall of a thin sheet; and a peel cover removably attached to the adhesive coating and holding the capsule on or over the pad, the top wall of the capsule having a central portion dented toward the capsule bottom wall to form a groove extending laterally between opposed side walls of the capsule, the lower end of the dented portion having a pair of gentle slants extending upwardly from the center of the dented portion toward the capsule side walls, each slant having an actuate sectional profile to form a blade so as to rupture the thin sheet of capsule bottom when a force is applied to the upper surface of the capsule.

12. A first-aid adhesive bandage according to claim 11 wherein the capsule is rectangular in plan view and has a top wall, side walls and a flange projecting horizontally outwardly from the lower peripheral end of the side walls.

13. A first-aid adhesive bandage according to claim 12 wherein the peel cover has an aperture permitting the top wall and side walls of the capsule to pass therethrough and the capsule is retained on or over the pad with the top wall and the side walls passed through the aperture and the flange of the capsule covered with and supported by the peel cover.

14. A first-aid adhesive bandage according to claim 12 wherein the peel cover consists of a pair of peel sheets superposed on each other, said upper peel sheet being formed with an aperture permitting the top wall of the capsule and the side walls thereof to pass therethrough and said lower peel sheet having an aperture through which the medicinal agent released from the capsule can flow into the pad, said capsule being retained on or over the pad such that the flange of the capsule is interposed between the upper and lower peel sheets with its top wall and the side walls passed through the aperture of the upper peel sheet.

15. A first-aid adhesive bandage according to claim 11 wherein said peel cover is made of plastics and formed integrally with the said capsule.

* * * * *